United States Patent [19]

Inoue et al.

[11] 4,215,213

[45] Jul. 29, 1980

[54] PROCESS FOR PRODUCING A GLYCOLIPID ESTER

[75] Inventors: Shigeo Inoue, Saitama; Yoshiharu Kimura, Ichikawa; Manzo Kinta, Funabashi, all of Japan

[73] Assignee: Kao Soap Co., Ltd., Tokyo, Japan

[21] Appl. No.: 962,693

[22] Filed: Nov. 21, 1978

[30] Foreign Application Priority Data

Feb. 17, 1978 [JP] Japan .................. 53-17400

[51] Int. Cl.$^2$ .................. C07H 15/06; C07H 3/04
[52] U.S. Cl. .................. 536/115; 536/4; 536/116; 536/119
[58] Field of Search .................. 536/115, 119, 116, 120, 536/4

[56] References Cited

U.S. PATENT DOCUMENTS

| | | | |
|---|---|---|---|
| 2,602,789 | 7/1952 | Schwartz et al. | 536/116 |
| 2,931,797 | 4/1960 | Gibbons et al. | 536/116 |
| 2,992,082 | 7/1961 | Ownby et al. | 536/119 |
| 3,585,185 | 6/1971 | Levis, Jr. et al. | 536/116 |
| 3,631,025 | 12/1971 | Martin | 536/119 |
| 3,634,397 | 1/1972 | Thompson et al. | 536/119 |
| 4,011,389 | 3/1977 | Langdon | 536/120 |

*Primary Examiner*—Johnnie R. Brown
*Attorney, Agent, or Firm*—Oblon, Fisher, Spivak, McClelland & Maier

[57] ABSTRACT

A process for producing a glycolipid ester represented by the formula,

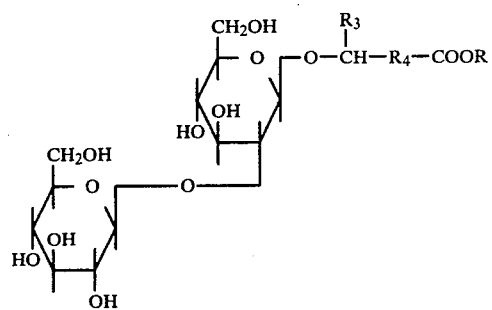

wherein $R_3$ represents a hydrogen atom or a methyl group, $R_4$ represents a saturated or unsaturated hydrocarbon group having 12 to 16 carbon atoms when $R_3$ is a hydrogen atom, $R_4$ represents a saturated or unsaturated hydrocarbon group having 11 to 15 carbon atoms when $R_3$ is a methyl group, and R represents a saturated or unsaturated alkyl group having 2 to 20 carbon atoms, which comprises subjecting Sophorolipid to methanolysis and methylation reactions by reaction with methanol in the presence of a strong acid to produce methyl 1-[(2'-O-$\beta$-D-glucopyranosyl-$\beta$-D-glucopyranosyl)oxy]-alkanoate and -alkenoate, and subjecting the resulting mixture to ester interchange by reaction with an alcohol represented by the formula,

ROH wherein R is the same as defined above.

10 Claims, No Drawings

PROCESS FOR PRODUCING A GLYCOLIPID ESTER

BACKGROUND OF THE INVENTION

1. Field of the Invention

This invention relates to glycolipid esters and in particular to a process for producing a glycolipid ester having surface activity and wax-like properties and represented by formula (I),

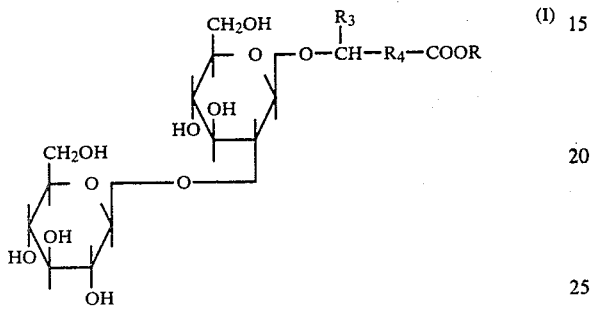

wherein $R_3$ represents a hydrogen atom or a methyl group, $R_4$ represents a saturated or unsaturated hydrocarbon group having 12 to 16 carbon atoms when $R_3$ is hydrogen, $R_4$ represents a saturated or unsaturated hydrocarbon group having 11 to 15 carbon atoms when $R_3$ is methyl, and R represents a saturated or unsaturated alkyl group having 2 to 20 carbon atoms.

2. Description of the Prior Art

Higher fatty acid esters of sucrose: (sugar esters) and higher fatty acid esters of anhydrosorbitol (Span) have been widely used as surface active agents, particularly in the field of emulsifying agents. Such known esters are formed via the ester bonding between the hydroxy group of the sugar moiety and the higher fatty acid, and the surface activities of these esters are regulated according to their ester values. Selective esterification of sugar at its desired position or positions is nearly impossible because many hydroxy groups exist in the sugar structure. In this situation, only mixtures of various ester isomers are utilized on an industrial basis. The hydrophilic properties of these esters are significantly decreased as the ester values increase because the esters are formed by esterification of the hydroxy groups in the sugar. Consequently, much difficulty is encountered with the emulsifying processes. Another problem is that the esters are chemically unstable by reason of the fact that the ester bonds of the hydroxy groups in the sugar and higher fatty acid are more easily hydrolyzed than those of the common fatty alcohol esters.

It has been reported by J. F. T. Spencer et al [Canadian Journal of Chemistry, 39, 846 (1961)] that great quantities of Sophorolipid are produced by culturing Torulopsis bombicola.

Sophorolipid is a mixture of the compounds represented by formulas (IIa) and (IIb),

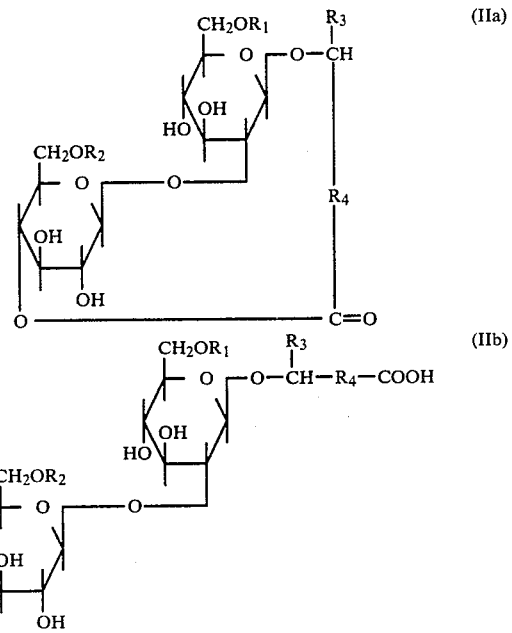

IIa-1: $R_1=R_2=COCH_3$
IIa-2: $R_1=COCH_3$, $R_2=H$
IIa-3: $R_1=H$, $R_2=COCH_3$
IIa-4: $R_1=R_2=H$
IIb-1: $R_1=R_2=COCH_3$
IIb-2: $R_1=COCH_3$, $R_2=H$
IIb-3: $R_1=H$, $R_2=COCH_3$
IIb-4: $R_1=R_2=H$ wherein $R_3$ and $R_4$ in formulas (IIa) and (IIb) are the same as defined above.

As can be seen from formulas (IIa) and (IIb), Sophoropilid is a mixture of many glycolipids, and its basic structure is of a [(2'-O-β-D-glycopyranosyl-β-D-glycopyranosyl)-oxy]-alkane acid or alkene acid which is obtained via the glycoside bonding between Sophorose and a long-chain fatty acid having a hydroxy group at the ω or ω-1 position.

The compound of the present invention possesses structural features which cannot be found in the conventional glycolipidtype surface active agents and which are characterized by the fact that a stable glycoside bond is formed by the hydroxyfatty acid and sugar and that the end group of the alkyl or alkenyl group is a reactive carboxyl group. The compound has a greater chemical stability than those containing the conventional ester bonds because the hydrophobic alkyl or alkenyl group is linked to the hydrophilic group or sugar via glycoside bonding. Moreover, the alkyl or alkenyl group which has hydrophobic properties, is occupied at its end by the reactive carboxyl group, and it is possible to produce glycolipids possessing surface activities and wax-like properties which have wide application by modification of the carboxyl groups only while leaving unmodified the hydroxy groups of the sugar moiety.

However, the production of the compound of formula (I) from Sophorolipid by fermentation involves some problems. Namely, Sophorolipid cannot be used as a starting material because it is a mixture of many homologs having a lactone ring, a free carboxyl group, acetyl groups and the like as shown in formulas (IIa)

and (IIb). Accordingly, compound of formula (IIb-4) should be first produced by eliminating the acetyl groups and releasing the carboxyl group without destruction of the carbon framework. The compound of formula (IIb-4) is a highly viscous substance peculiar to a sugar compound and is very difficult to obtain by means of conventional methods.

When Sophorolipid is forcibly dispersed in water, and an acid or alkali is added to the resulting suspension in an amount necessary for normal hydrolysis of the ester bond, part of the deacetylated or deacylated compound, which is subject to partial hydrolysis, acts as an emulsifying agent by incorporating the unreacted substances into micelles against continued attack by the remaining acid or alkali, thereby resulting in incomplete hydrolytic action. For instance, the reaction proceeds to an extent of only about 50%, even if a given amount of potassium hydroxide (0.25 part per one part of Sophorolipid) is added to an aqueous solution containing 20% of Sophorolipid, and the resulting solution is hydrolyzed with heating for 6 hours. When hydrochloric acid is used in an amount of 5% instead of the alkali catalyst, hydrolysis is as incomplete as in the case where the alkali catalyst is employed, and partial cleavage of the glycosyl ether bond is caused as well as damage to the basic structure.

If the reaction is completed under the above conditions, potassium hydroxide should be used in an amount of 0.25 part per one part of Sophorolipid, which is an extremely great amount of base which is uneconomical, and it is nearly impossible to separate the compound of the formula (IIb-4) which forms from the reaction solution by any industrially acceptable process. One reason is that the compound of formula (IIb-4) is readily soluble in water, and can be only dissolved in lower alcohols such as methanol and ethanol or special expensive organic solvents such as pyridine, dimethylsulfoxide or dimethylformamide which would otherwise create a serious obstacle to safety. As another reason, such compounds have a viscosity of more than 100,000 cps at room temperature. Since potassium acetate which simultaneously forms is also readily soluble in water and alcohols, it is necessary to forcibly eliminate water and extract the potassium acetate with any one of those nitrogen-containing solvents, and subsequently distill off the solvent so that the compound of the formula (IIb-4) may be separated. This process is unacceptable from an industrial standpoint. It is not impossible but very difficult to obtain the compound of the present invention merely by reacting the free carboxyl group of the compound of the formula (IIb-4) with methanol because this compound is highly viscous. In addition, the glycosyl ether bond is cleaved under strongly acidic conditions since there is no proper solvent capable of dissolving the compound.

With the above-noted difficulties in mind, studies have been conducted and it has been found that an hydrous Sophorolipid of a low viscosity can be obtained by adding a small amount of at least one polyhydric alcohol represented by formulas (III) or (IV),

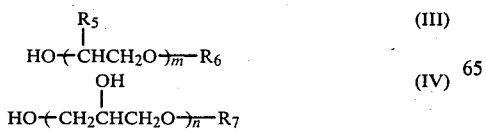

wherein $R_5$ represents a hydrogen atom or a methyl group, $R_6$ and $R_7$ represent a hydrogen atom or an alkyl group having 1 to 5 carbon atoms, and m and n represent integers from 1 to 6, to hydrated Sophorolipid which is a fermentation product of *Torulopsis bombicola*, and distilling off water under reduced pressure by application of heat. Such finding is disclosed in a co-pending application Ser. No. 928,964.

The present inventors have made an attempt to subject the above noted Sophorolipid of a lower viscosity to alcoholysis to deacetylate and cleave its lactone ring, and at the same time, esterify the free carboxyl group. As a result of this attempt, it has been found that the reaction is very slow with the use of an alcohol having 2 or more carbon atoms and, that, for instance, ethanol requires an extended period of reaction time by a factor of approximately 110 times that of methanol, although methanolysis and methylation proceed rather rapidly to yield a compound wherein R in the formula (I) is a methyl group. In the reaction over such a prolonged period of time, acid attacks and cleaves the glycoside bond, thereby resulting in damaged basic structure. The use of a long-chain alcohol forms its acetate having a high boiling point by alcoholysis, which is distilled off with much more difficulty than methyl acetate and cannot be separated successfully by any other fractional method. Thus, such a prior art method cannot produce a highly pure compound of the formula (I) on an industrial basis.

The present inventors have made continued studies on the solution of the above difficulties and have found that the compound of formula (I) can be obtained in a high purity and in high yield by producing, from Sophorolipid, methyl-[(2'-O-β-D-glucopyranosyl-β-D-glucopyranosyl)oxy]-alkanoate and -alkenoate of the formula (I) wherein R is a methyl group, and subjecting the resulting compound to an ester interchange reaction with an alcohol having 2 to 20 carbon atoms.

SUMMARY OF THE INVENTION

The invention provides a process for producing a glycolipid ester of the formula (I), which comprises subjecting Sophorolipid represented by formulas (IIa) and (IIb) to methanolysis and methylation reactions by reaction with methanol in the presence of a strong acid to produce methyl-[(2'-O-β-D-glucopyranosyl-β-D-glucopyranosyl)oxy]-alkanoate and -alkenoate represented by the formula (I), wherein R is a methyl group (hereinafter referred to as a glycolipid methyl ester) and an acetic acid methyl ester, distilling off the acetic acid methyl ester together with methanol as an azeotropic mixture, and subjecting the resulting mixture to ester interchange by reaction with an alcohol represented by the formula, ROH, wherein R is the same as defined above.

The glycolipid methyl ester is produced from Sophorolipid by adding at least one polyhydric alcohol represented by formulas (III) or (IV) to hydrated Sophorolipid, distilling off water under reduced pressure to produce the Sophorolipid-polyhydric alcohol system having a lower viscosity, and reacting the system with methanol in the presence of a strong acid.

DETAILED DESCRIPTION OF THE PREFERRED EMBODIMENTS

Suitable polyhydric alcohols which are useful in the invention include, for example, ethyleneglycol, ethyleneglycol monomethyl ether, ethyleneglycol monoethyl ether, ethyleneglycol monopropyl ether, ethyleneglycol, diethyleneglycol monomethyl ether, diethyleneglycol monoethyl ether, diethyleneglycol monobutyl ether, polyethyleneglycol having an average molecular weight of 150 to 280, propyleneglycol, dipropyleneglycol, tripropyleneglycol, tetrapropyleneglycol, pentapropyleneglycol, hexapropyleneglycol, propyleneglycol monomethyl ether, propyleneglycol monoethyl ether, propyleneglycol monopropyl ether, propyleneglycol monobutyl ether, dipropyleneglycol monomethyl ether, dipropyleneglycol monoethyl ether, tripropyleneglycol monomethyl ether and the like represented by formula (III) as well as, glycerine, polyglycerine, block-polymers of ethyleneglycol and propyleneglycol and the like represented by the formula (IV). The polyhydric alcohols may be used singly or in combination.

The use of an alkaline agent instead of an acid results in the formation of 30 to 40% by weight of the compound of the formula (I) wherein R is hydrogen because of the existence of the compound of the formula (IIb) in Sophorolipid which amounts to 30 to 40% by weight, and 60 to 70% by weight of the methyl ester which results from to the cleavage of the lactone ring. Consequently, the reaction is not preferable in the presence of an alkali.

Methanolysis hardly proceeds with the use of a weak acid such as phosphoric acid. A strong acid such as hydrochloric acid, sulfuric acid or nitric acid allows for rapid deacetylation and cleavage of the lactone ring, but the glycosyl ether bond is attacked under normal conditions of methylation whereby the basic structure is damaged. Because of these disadvantages, an attempt has been made to find the optimal reaction conditions under which alcoholysis and methylation are perfectly completed without the glycosyl ether bond being damaged. In the studies leading to this invention, the present inventors have discovered that the reaction proceeds advantageously with a strong acid such as hydrochloric acid, sulfuric acid or nitric acid in a concentration of from 0.05 to 0.50 N at a temperature of less than 45° C., and produces a single glycolipid methyl ester of the formula (I) wherein R is a methyl group. It is to be noted that cleavage of the glycosyl ether bond is induced by using a strong acid in a concentration of more than 0.50 N and that such cleavage proceeds rapidly at a reaction temperature above 45° C.

The reaction is carried out with stirring for about 90 minutes, and the resulting mixture is subjected to thin layer chromatography. The reaction is regarded as having become complete when only one Sophorolipid spot is observed on the thin layer.

After being allowed to cool to room temperature, the reaction solution is neutralized with sodium hydroxide, potassium hydroxide or an alkali metal methylate. The neutral salt which forms is filtered off, and the methyl acetate produced from the mother liquor and excess methanol are distilled off as an azeotropic mixture under normal pressure to such an extent that methanol remains in the residue in an amount of about 10% by weight of the reaction product. The thus obtained reaction mixture is preferably used for subsequent reactions without any further treatment.

Ester interchange is carried out by reacting the glycolipid methyl ester with a desired alcohol in the presence of an alkaline agent. Of the alkali agents sodium hydroxide, potassium hydroxide and or alkali metal methylate are preferably used in an amount of 0.2 to 1.0% by weight of the reaction product containing about 10% of methanol. The alcohol is preferably used in a molar ratio ranging from 1.1 to 1.2 relative to the glycolipid methyl ester. For the best results, the reaction is conducted with stirring at 70° to 80° C. under a reduced pressure of 100 to 200 mmHg while distilling off methanol as a solvent and the methanol produced by ester interchange. The reaction is usually completed within from 30 minutes to 2 hours to afford the compound of formula (I) in a high yield.

The thus obtained compound according to this invention has both surface activity and wax-like properties, and exhibits the following superior characteristics in comparison to sugar esters of the conventional typical glycolipidtype surface active agents.

(1) Among the sugar esters, the monoester is about 18 to 14, the diester about 7, and the triester about 3 to 4 in their HLB values. The HLB value variations are relatively small in the sugar esters. On the other hand, the glycolipid ester has an HLB value of more than 20, and the compound of the formula (I) wherein R is $C_2H_5$ or $C_{18}H_{35}$ has an HLB of 6. Thus, various glycolipid esters having a wide range of HLB values can be obtained by changing the number of carbon atoms of the alcohols.

(2) While the surface tension is of the same degree in both types of compound, the glycolipid ethyl ester is about twice as high in forming power as the sugar ester (monooleate) and is also superior in detergency to the sugar ester.

(3) In terms of the emulsifying ability, both types of compounds give different emulsions. The glycolipid methyl ester forms a homogeneous emulsion containing extremely fine particles and possesses the same emulsifying ability as the sugar ester in less than half the amount of the sugar ester.

(4) The glycolipid methyl ester has good miscibility with various fats and oils, and hydrocarbon-type substances. This ester acts as an improving agent for fats and oils and the like, and is useful as a wax-like material.

(5) The glycolipid methyl ester possesses excellent hydroscopic properties and water-keeping abilities comparable to that of lanolin as well as good wet-permeability because of its Sophorose residue. The ester also has wax-like is because of the presence of the long-chain hydrophobic group. Therefore, when applied as an emulsifying agent, a wet-keeping agent or a moisturizer for cosmetics, the ester exerts a skin-protecting and feeling-improving effect which cannot be found in the conventional esters.

(6) The glycolipid methyl ester can be easily treated because of good solubility in water and many organic solvents and is chemically stable. Consequently, the ester finds wide application.

The glycolipid methyl ester according to the invention possesses the above-mentioned superior properties; therefore, it may be utilized as a base or improvement additive for various cleansers, and fat and oil products for use with painting, printing, fiber processing, metal processing, stationery, cosmetics, drugs, agricultural chemicals, luster preservation, synthetic resins, paper manufacturing, machinery, leather and the like.

The invention is illustrated below in further detail with reference to some non-limiting Examples.

EXAMPLE 1

Production of [(2'-O-β-D-glucopyranosyl-β-D-glucopyranosyl)-oxy]-alkane acid and -alkene acid methyl esters:

(1) To a mixture of 1,500 g of glucose, 75 g of a yeast extract and 15 g of urea was added water to adjust the whole volume to 15 l, and the resulting mixture was sterilized and used as a fermentation liquid. This liquid was inoculated with 150 ml of *Torulopsis bombicola* which had been cultured on the same medium as above at 30° C. for 48 hours. The fermentation was started with stirring at a speed of 300 rpm and an aeration of 0.33 VVM at 20° C. The culturation was conducted for 24 hours after the inoculation of the microorganisms, and 150 g of a tallow oil was added at intervals of 24 hours. The added tallow oil amounted to 900 g. After the final addition, culturing was continued for 24 hours. The culturation time amounted to 168 hours. A Sophorolipid layer which precipitated at the bottom of the fermentor was collected by decantation to give 1,300 g of Sophorolipid in a paste form at room temperature which had a water content of about 50%.

(2) 100 g of the thus obtained Sophorolipid and 2.5 g of polypropyleneglycol having an average molecular weight of 200 were placed in a 200 ml round bottom flask equipped with a stirrer and a Liebig condenser. The mixture was evaporated with stirring at 80° C. in an oil bath under a reduced pressure of 250 mmHg to eliminate water. After the evaporation for about 2 hours, water was completely distilled off, and the water content was found to be less than 1%.

(3) To the Sophorolipid-polypropyleneglycol solution were added 150 g of methanol and then 2.5 g of sufuric acid. The resulting mixture was reacted at 40° C.±2° C. for 90 minutes. The reaction progress was observed by thin layer chromatography on silica gel [solvent: chloroform-methanol-acetic acid (75:20:5)], and the reaction was regarded as having been complete when many spots shown by raw Sophorolipid converged on the thin layer chromatograph.

After the completion of the reaction, the mixture was neutralized with potassium hydroxide and filtered through filter paper. The filtrate was placed in a round bottom flask equipped with a Liebig condenser, and methanol and methyl acetate were distilled off to give 48 g of the residue as a brown paste which consisted of 94% of [(2'-O-β-D-glucopyranosyl)-β-D-glucopyranosyl)-oxy]-alkane acid and -alkene acid methyl ester and polypropylene glycol. This residue was purified by column chromatography on silica gel, and there were obtained pure [(2'-O-β-D-glucopyranosyl-β-D-glucopyranosyl)oxy]-alkane acid and -alkene acid methyl esters.

IR (cm$^{-1}$): 1740 (>C=O ester); 1380~3200 (—OH sugar); 900~750 (glucopyranose ring).

NMR [δ(pyridine)]: 1.1~1.6 (—CH$_2$—CH$_2$—); 3.6 (—O—CH$_3$); 3.5~5.0 (sugar); 5.5 (—CH=CH— unsaturated fatty acid).

Oil Characterization Analysis:
Acid value: 0
Hydroxy value: 615
Saponification value: 88
Ester value: 87

This product was degraded in a 5 N hydrochloric acidmethanol solution to give 2 moles of the methyl glycoside and 1 mole of the hydroxyfatty acid methyl ester, which were quantitatively analyzed by gas chromatography.

EXAMPLE 2

Production of various esters [(2'-O-β-D-glucopyranosyl-β-D-glucopyranosyl)oxy]-alkane acid and -alkene acid:

To the mixture of methyl ester-polypropyleneglycol obtained in Example 1 were added 1.1 moles of an aliphatic alcohol relative to one mole of the methyl ester, and the resulting mixture was subjected to ester interchange by adding 0.5% by weight of sodium methylate. The methanol formed during the reaction was distilled off under normal or reduced pressure to obtain various desired aliphatic alcohol esters. The following are the preparation methods for some typical derivatives.

(1) Ethyl ester

To 20 g of the methyl ester-polypropyleneglycol obtained in Example 1 was added 20 g of ethanol to obtain a homogeneous solution to which was added 0.1 g of sodium methylate. The ester interchange reaction was conducted at 70° C. while distilling off ethanol and methanol which gradually formed during the course of reaction. The mixture was neutralized with a sulfuric acidethanol solution and filtered. The filtrate was evaporated to eliminate ethanol to give 19 g of an ethyl ester. The reaction progress was observed by measuring the area ratio of the gas chromatographic peaks of the methyl and ethyl esters obtained on a 3% silicon JXR-chromosolve W column having a particle size of 60–80 mesh and a helium gas stream of 0.6 kg/cm$^2$ at a column oven temperature of 310° C. with a hydrogen flame detector using a trimethylsililated product obtained with a trimethylsililating agent. The reaction was terminated when the methyl ester peak disappeared.

(2) Octyl ester

To 20 g of the methyl ester-polypropyleneglycol obtained in Example 1 was added 4.2 g of octyl alcohol, and to the mixture was added 5 g of methanol to obtain the homogeneous solution to which was then added 0.1 g of sodium methylate. The greater part of the methanol was distilled off at 70° C., and the ester interchange reaction was conducted while distilling off the formed methanol with stirring under a reduced pressure of 250 mmHg. The reaction progress was observed by gas chromatography as described above, and the reaction was terminated when the peak of the methyl ester disappeared. The mixture was neutralized with a fixed amount of citric acid to obtain 24 g of an octyl ester.

(3) Lauryl ester

To 20 g of the methyl ester-polypropyleneglycol obtained in Example 1 were added 6.1 g of lauryl alcohol, 5 g of methanol and then 0.1 g of sodium methylate. Thereafter, the same procedure as in the above process (2) was repeated to yield 26 g of a lauryl ester.

(4) Oleyl ester

To 20 g of the methyl ester-polypropyleneglycol obtained in Example 1 were added 8.9 g of oleyl alcohol, 5 g of methanol and then 0.1 g of sodium methylate. Thereafter, the same procedure as described above for process (2) was repeated to afford 29 g of the oleyl ester.

The thus obtained octyl ester, lauryl ester and oleyl ester were purified by column chromatography on silica gel, and the resulting pure products were all white paste substances. The IR absorption spectra and NMR spectra of these products were the same with the exception of the differences of the methyl ester spectra and of the absorption strength of the methylene groups. The octyl ester was decomposed in a 5 N hydrochloric acid-methanol solution to obtain 2 moles of the methyl glycoside, 1 mole of the hydroxyfatty acid methyl ester and 1 mole of the octyl alcohol. Under the same conditions, the lauryl ester yielded 2 moles of the methyl glycoside, 1 mole of the hydroxy fatty acid methyl ester and 1 mole of the lauryl alcohol, and the oleyl ester gave 2 moles of the methyl glycoside, 1 mole of the hydroxy fatty acid methyl ester and 1 mole of the oleyl alcohol.

These products were further ascertained by their hydroxy values, acid values, saponification vales and ester values obtained by oil analyses.

| Oil Characterization Values of Various Esters | | | | | |
|---|---|---|---|---|---|
| | | Hydroxy value | Acid value | Saponification value | Ester value |
| Octyl ester | Calculated | 534.7 | 0 | 76.3 | 76.3 |
| | Found | 530.2 | 0 | 77.5 | 77.5 |
| Lauryl ester | Calculated | 497.0 | 0 | 71.9 | 71.9 |
| | Found | 503.2 | 0 | 73.0 | 73.0 |
| Oleyl ester | Calculated | 450.4 | 0 | 64.3 | 64.3 |
| | Found | 445.0 | 0 | 66.1 | 66.1 |

EXAMPLE 3

The surface activities of the compounds produced in Example 2 are as shown in the following table.

| | Surface tension (dyne/cm$^2$) | HLB (Davis's method) |
|---|---|---|
| Methyl ester | 40.0 | >20 |
| Ethyl ester | 39.5 | >20 |
| Propyl ester | 38.0 | >20 |
| Butyl ester | — | >20 |
| Hexyl ester | — | 20 |
| Octyl ester | — | 17 |
| Decyl ester | — | 15 |
| Lauryl ester | — | 13 |
| Myristyl ester | — | 10 |
| Palmityl ester | — | 8 |
| Stearyl ester | — | 6 |
| Oleyl ester | — | 7 |

What is claimed is:

1. A process for producing a glycolipid ester represented by the formula,

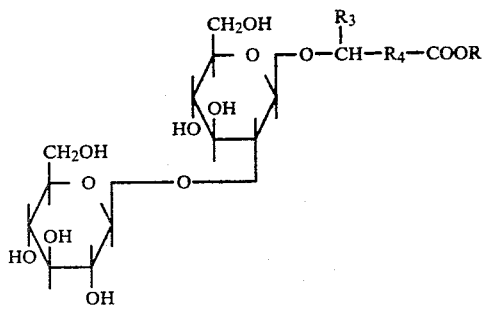

wherein $R_3$ represents hydrogen or methyl, $R_4$ represents a saturated or unsaturated hydrocarbon group having 12 to 16 carbon atoms when $R_3$ is a hydrogen atom, or $R_4$ represents a saturated or unsaturated hydrocarbon group having 11 to 15 carbon atoms when $R_3$ is a methyl group, and R represents a saturated or unsaturated alkyl group having 2 to 20 carbon atoms, which comprises: subjecting Sophorolipid to methanolysis and methylation by reacting said Sophorolipid with methanol in the presence of a strong acid thereby forming an ester mixture of methyl 1-[(2'-O-β-D-glucopyranosyl-β-D-glucopyranosyl)oxy]-alkanoate and -alkenoate; and subjecting said mixture to ester interchange by reacting said ester mixture with an alcohol represented by the formula

ROH wherein R is the same as defined above.

2. A process for producing a glycolipid ester represented by the formula,

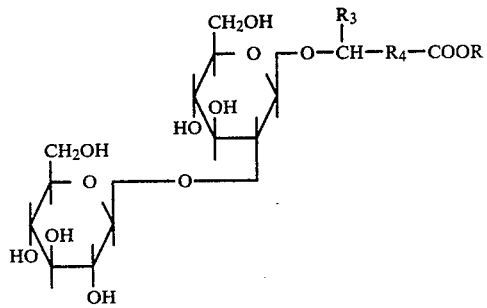

wherein $R_3$ represents hydrogen or methyl, $R_4$ represents a saturated or unsaturated hydrocarbon group having 12 to 16 carbon atoms when $R_3$ is a hydrogen atom or $R_4$ represents a saturated or unsaturated group having 11 to 15 carbon atoms when $R_3$ is a methyl group, and R represents a saturated or unsaturated alkyl group having 2 to 20 carbon atoms, which comprises: adding at least one polyhydric alcohol represented by formulas (III) or (IV),

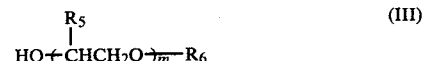
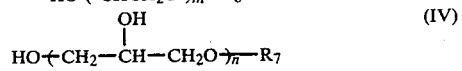

wherein $R_5$ represents hydrogen or methyl, $R_6$ and and $R_7$ represent hydrogen or an alkyl group having 1 to 5 carbon atoms, and m and n represent integers from 1 to 6, to hydrated Sophorolipid; removing water by distillation from the mixture under reduced pressure; and subjecting the resulting Sophorolipid-polyhydric alcohol system to methanolysis and methylation by reaction of said system with methanol in the presence of a strong acid to produce methyl-[2'-O-β-D-glucopyranosyl-β-D-glucopyranosyl)oxyl]-alkanoate and -alkenoate; and subjecting the resulting mixture to ester interchange by reaction with an alcohol represented by the formula,

ROH wherein R is the same as defined above.

3. The process of claim 1 or 2, wherein the strong acid is used in a concentration of from 0.05 to 0.50 N.

4. The process of claim 1 or 2, wherein the methanolysis and methylation reactions are conducted at a temperature below 45° C.

5. The process of claim 1 or 2, wherein the ester interchange is conducted in the presence of an alkaline agent.

6. The process of claim 1 or 2, wherein said strong acid is hydrochloric acid, sulfuric acid or nitric acid.

7. The process of claim 1 or 2, wherein said polyhydric alcohol is selected from the group consisting of ethyleneglycol, ethyleneglycol monomethyl ether, ethyleneglycol monoethyl ether, ethyleneglycol monopropyl ether, diethyleneglycol, diethyleneglycol monomethyl ether, diethyleneglycol monoethyl ether, diethyleneglycol monobutyl ether, polyethyleneglycol having an average molecular weight of 150 to 280, propyleneglycol, dipropyleneglycol, tripropyleneglycol, tetrapropyleneglycol, pentapropyleneglycol, hexapropyleneglycol, propyleneglycol monomethyl ether, propyleneglycol monoethyl ether, propyleneglycol monopropyl ether, propyleneglycol monobutyl ether, dipropyleneglycol monomethyl ether, dipropyleneglycol monoethyl ether, and tripropyleneglycol monomethyl ether.

8. The process of claim 1 or 2, wherein an alkali agent selected from the group consisting of sodium hydroxide, potassium hydroxide and alkali metal methylate is employed in said ester interchange reaction.

9. The process of claim 8, wherein said alkali agent is present in an amount of 0.2 to 1.0 wt % relative to the reaction product containing about 10% methanol.

10. The process of claim 1 or 2, wherein said ester interchange reaction is conducted at a temperature of 70° to 80° C.

* * * * *

UNITED STATES PATENT AND TRADEMARK OFFICE
CERTIFICATE OF CORRECTION

PATENT NO. : 4,215,213

DATED : July 29, 1980

INVENTOR(S) : Shigeo Inoue et al

It is certified that error appears in the above-identified patent and that said Letters Patent are hereby corrected as shown below:

In column 1, in line 37, ":" after "sucrose" should be deleted; line 63, "39" should be underlined; and in line 65, "Torulopsis bombicola" should be italicized.

In column 2, in line 38, "Sophoropilid" should be spelled --Sophorolipid--; in lines 39 and 40, "glycopyranosyl" should be spelled --glucopyranosyl--; and in line 53, "the" after "because" should be deleted.

In column 3, in line 1, --the-- should be inserted before "compound"; in line 63, the identification mark "(III)" should be moved to line 64; and in line 66, the identification mark "(IV)" should be moved to line 67.

In column 4, line 15, "," after "and" should be deleted.

In column 5, line 67, "and" should be deleted.

In column 7, line 45, ")" should be deleted; and in

UNITED STATES PATENT AND TRADEMARK OFFICE
CERTIFICATE OF CORRECTION

PATENT NO. : 4,215,213

DATED : July 29, 1980

INVENTOR(S) : Shigeo Inoue et al

It is certified that error appears in the above-identified patent and that said Letters Patent are hereby corrected as shown below:

line 65, "acidmethanol" should be --acid methanol--.

In column 8, line 24, "acidmethanol" should be --acid methanol--.

In column 9, lines 3 and 4, "acidmethanol" should be --acid methanol--; in line 13, "vales" should be spelled --values--; and in lines 15 to 25 (Table of Example 2), the heading "Hydroxy value" should be displaced to the right until it heads the column of numbers that begins with "534.7".

The term of this patent subsequent to August 5, 1997, has been disclaimed.

Signed and Sealed this

Tenth Day of March 1981

[SEAL]

Attest:

RENE D. TEGTMEYER

Attesting Officer

Acting Commissioner of Patents and Trademarks